US006720311B2

(12) United States Patent
Tsai (10) Patent No.: US 6,720,311 B2
(45) Date of Patent: Apr. 13, 2004

(54) POLYPEPTIDE FOR THE TREATMENT OF CANCER AND A METHOD FOR PREPARATION THEREOF

(76) Inventor: David Tsai, 18 Technology Dr., Suite 170, Irvine, CA (US) 92618

( * ) Notice: Subject to any disclaimer, the term of this patent is extended or adjusted under 35 U.S.C. 154(b) by 1 day.

(21) Appl. No.: 10/145,682

(22) Filed: May 14, 2002

(65) Prior Publication Data

US 2003/0027767 A1 Feb. 6, 2003

Related U.S. Application Data

(63) Continuation-in-part of application No. 09/902,208, filed on Jul. 9, 2001, which is a continuation-in-part of application No. 09/414,136, filed on Oct. 7, 1999, now Pat. No. 6,258,779, which is a continuation-in-part of application No. 09/149,878, filed on Sep. 8, 1998, now Pat. No. 5,994,298, which is a continuation-in-part of application No. 08/993,432, filed on Dec. 18, 1997, now abandoned.

(51) Int. Cl.$^7$ .......................... A61K 38/08; C07K 7/06; C07K 7/08
(52) U.S. Cl. ............................... 514/44; 514/6; 514/8; 514/15; 530/328; 530/400
(58) Field of Search .......................... 514/6, 8, 15, 44; 530/328, 400

(56) References Cited

U.S. PATENT DOCUMENTS

| | | |
|---|---|---|
| 5,449,757 A | 9/1995 | Serrero |
| 5,500,432 A | 3/1996 | Nicolaou ............... 514/281 |
| 5,550,019 A | 8/1996 | Reed ..................... 435/6 |
| 5,591,717 A | 1/1997 | Rojko ................... 514/12 |
| 5,604,113 A | 2/1997 | White ................... 435/29 |
| 5,624,808 A | 4/1997 | Thompson .............. 435/7.24 |
| 5,639,727 A | 6/1997 | Little et al. |
| 5,650,491 A | 7/1997 | Reed .................... 530/350 |
| 5,656,725 A | 8/1997 | Chittenden ............. 530/324 |

FOREIGN PATENT DOCUMENTS

WO  WO 86/02651  5/1986

OTHER PUBLICATIONS

Dziegielewska, K.M., et. al., Fetuin, pp. 16–17, (R.G. Landes Co. 1995).
Wang et al., Oncogene, vol. 15 pp. 143–157, Sep. 1997.
Lin, et al., "In Vitro Apoptosis in the Human Hepatoma Cell Line Induced by Transforming Growth Factor B,", Cancer Research, 52, 385–388 (1992).
Grotendorst, et al., "Attachment of Smooth Muscle Cells to Collagen and their Migration toward platelet–derived growth factor", Proc. Natl. Acad. Sci. USA, vol. 78, No. 6, pp. 3669–3672 (1991).
Wiley, et al. . "Identification and Characterization of a new Member of the TNF Family that Induces Apoptosis", Immunity vol. 3, 673–682 (1995).
Kawakami et al., "Cachectin/TNF Kills or Inhibits the Differentiation of 3T3–L1 Cells According to Developmental Stage". J. of Cellular Physiology 138:1–7 (1989).
Krammer, et al., "Apoptosis in the APO–1 system", Apoptosis: The Molecular Basis of Cell Death, pp. 87–99 (1991).
von Bulow, et al., "Human fetuin/a,HS glycoprotein in colloid and parenchymal cells in human fetal pituitary gland", Histochemistry, (1993) 99:13–22.
Spiro, "Studies on Fetuin, a glycoprotein of Fetal Serum" The Journal of Biological Chemistry, vol. 235, No. 10, pp. 2860–2869.
Grant, et al., "Effects of Epidermal Growth Factor, Fibroblast Growth Factor, and Transforming Growth Factor–B on Cornmeal Cell Chemotaxis", Investigative Ophthalmology & Visual Science, vol. 33, No. 12 (1992).
Yang, et al., "Human a –HS–glycoprotein/bovine fetuin homologue identification and development regulation of the gene", Biochemica et Biophysica Acta 1130 (1992) 149–156.
Yoshioka, et al., The Completer Amino Acid Sequence of the A–chain of Human Plasma a$_2$HS–glycoprotein, The Journal of Biological Chemistry, vol. 261, No. 4, pp. 1665–1676 (1986).
Gejyo, et al., "Characterization of the B–Chain of Human Plasma a 2 HS–Glycoproein", The Journal of Biological Chemistry, vol. 258 No. 8, pp. 4966–4971 (1983).
Kerr, J.F.R. and Searle, J., A Suggested Explanation for the Paradoxically slow growth rate of basal–cell Carcinomas . . . , J. Path., vol. 107, p.41–44, (1971).
Michaelson, J., Cell Selection in Development, Biol. Rev. (1987), vol. 62, p. 115–139, Great Britain.
Wyllie, A.H., et. al., Cell Death: The Significance of Apoptosis, International Review of Cytology, vol. 68, pp. 251–306, Academic Press, 1980.
Cope, F., et. al., Apoptosis: The Molecular Basis of Cell Death, Cold Spring Harbor Laboratory Press, pp. 61–86, 1991; Carciogenesis and Apoptosis: Paradigms.
Su, et.al., FASEB J. vol. 8, No. 4, Abstract No. 1257, p. A218.
Dziegielewska, K.M., et. al., Fetuin, "Structure of the Fetuins," Chap. 2, pp. 11–42 (R.G. Landes Co.1995).

Primary Examiner—Bennett Celsa
(74) Attorney, Agent, or Firm—Trojan Law Offices (57) ABSTRACT

This invention characterizes the specific peptide fragment derived from specially prepared zinc charged fetuin and a method of preparation thereof, wherein the fragment was found to contain an apoptosis-inducing activity. Specifically, the amino acid sequence of this peptide is H-T-F-S-G-V-A-S-V-E and correlates to amino acid no. 300-309 of fetuin, referred to herein as Fetuin Peptide Fragment (FPF 300-09). FPF 300-09 strongly induced apoptosis in LNCaP (prostate cancer) and HT-29 (colon cancer) cells without affecting CCD 18 Co (normal colon) cells. The in vitro tissue culture study demonstrated that the FPF 300-09 is more potent than the parent molecule (full-length zinc charged fetuin) in inducing apoptosis. FPF 300-09 has a LD$_{50}$ of 0.3–0.4 μM, while the LD$_{50}$ for zinc-charged fetuin is 3–10 μM.

7 Claims, 6 Drawing Sheets

| Group | Number of Mice | Dosage | Survivors (days) | Increased Life Span (ILS) |
|---|---|---|---|---|
| I | 10 | 0.002 ml fetuin | 1 (31) | 29% |
| II | 10 | 0.02 ml fetuin | 1 (29) | 17.2 % |
| III | 10 | 0.2 ml fetuin | 8 (58) | 141 % |
| IV | 10 | 0.5 ml saline | 0 (24) | --- |

Fig. 1

| Type of Fetuin | Amount Required to Reach $LD_{50}$ |
|---|---|
| Fetuin + Zn | 130 μM |
| Supercharged Zinc Fetuin | 14.3 μM |

Fig. 2

| Type of Fetuin | Amount Required to Reach $LD_{50}$ |
|---|---|
| Fetuin + Zn | 60 μM |
| Supercharged Zinc Fetuin | 19.6 μM |

| Experiment | Sample | Apoptosis (%) |
|---|---|---|
| 1 | Filtrate (10 µl) | 92% |
| | Filtrate (10 µl) + proteinase K | 50% |
| 2 | Filtrate (5 µl) | 35% |
| | Filtrate (5 µl) + proteinase K | 0% |
| 3 | Filtrate (10 µl) | 75% |
| | Filtrate (10 µl) + proteinase K | 0% |

FIG. 13

| Fetuin | $LD_{50}$ |
|---|---|
| Zinc Charged Fetuin (full length) | $LD_{50}$ = 3-10 µM |
| Fetuin Fragment (amino acid no. 300-309) | $LD_{50}$ = 0.3-0.4 µM |
| Fetuin Fragment (amino acid no. 300-307) | $LD_{50}$ >> 1 mM |
| Fetuin Fragment (amino acid no. 310-317) | $LD_{50}$ >> 1 mM |

FIG. 12

POLYPEPTIDE FOR THE TREATMENT OF CANCER AND A METHOD FOR PREPARATION THEREOF

CLAIM OF PRIORITY

This application is a continuation-in-part to U.S. Ser. No. 09/902,208 (filed Jul. 9, 2001), which is a continuation-in-part to U.S. Ser. No. 09/414,136 (filed Oct. 7, 1999), now U.S. Pat. No. 6,258,779 (issued Jul. 10, 2001), which is a continuation-in-part to U.S. Ser. No. 09/149,878 (filed Sep. 8, 1998), now U.S. Pat. No. 5,994,298 (issued Nov. 30, 1999), which is a continuation-in-part to U.S. Ser. No. 08/993,432 (filed Dec. 18, 1997) now abandoned.

BACKGROUND OF THE INVENTION

Human beings have had a long battle against cancer. Because the disease is so widespread, manifests itself in so many different ways and is so relentless, the potential market for effective cancer therapies is enormous. It is estimated that 10 million people in the U.S. either have or have had cancer. The National Cancer Institute (NCI) projects that in 1995, some 1.2 million new cases of cancer will be diagnosed in the United States, and that 538,000 people will die of the disease. Cancer is currently treated, with a low degree of success, with combinations of surgery, chemotherapy and radiation. The reason of the low degrees of success in cancer chemotherapy is as the following: current chemotherapeutic approaches target rapidly dividing tumor cells. This approach is ineffective when the cancer is dormant or growing slowly. Such treatments also affect other, noncancerous cells that divide rapidly, causing harmful side effects.

Only in the last several years has a new approach emerged in the battle against cancer. This approach is based on the newly discovered biological phenomenon called "Apoptosis". Apoptosis is also called "programmed cell death" or "cell suicide". (Krammer, et al., "Apoptosis in the APO-1 System", Apoptosis: The molecular Basis of Cell Death, pp. 87–99 Cold Spring Harbor Laboratory Press, 1991). In contrast to the cell death caused by cell injury, apoptosis is an active process of gene-directed, cellular self-destruction and that it serves a biologically meaningful function. (Kerr, J. F. R and J. Searle J. Pathol. 107:41, 1971). One of the examples of the biologically meaningful functions of apoptosis is the morphogenesis of embryo. (Michaelson, J. Biol. Rev. 62:115, 1987). Just like the sculpturing of a sculpture, which needs the addition as well as removal of clay, the organ formation (Morphogenesis) of an embryo relies on cell growth (addition of clay) as well as cell death (removal of clay). As a matter of fact, apoptosis plays a key role in the human body from the early stages of embryonic development through to the inevitable decline associated with old age. (Wyllie, A. H. Int. Rev. Cytol. 68:251, 1980). The normal function of the immune, gastrointestinal and hematopoietic system relies on the normal function of apoptosis. When the normal function of apoptosis goes awry, the cause or the result can be one of a number of diseases, including: cancer, viral infections, auto-immune disease/allergies, neurodegeneration or cardiovascular diseases. Because of the versatility of apoptosis involved in human diseases, apoptosis is becoming a prominent buzzword in the pharmaceutical research field. Huge amounts of time and money are being spent in an attempt to understand how it works, how it can be encouraged or inhibited and what this means for practical medicine. A handful of companies have been formed with the prime direction of turning work in this nascent field into marketable pharmaceutical products. The emergence of a core of innovative young companies combined with the tentative steps being taken by established industrial players are certain to make apoptosis research one of the fastest-growing and most promising areas of medical study of the 1990's.

The idea that cancer may be caused by insufficient apoptosis merged only recently (Cope, F. O. and Wille, J. J., "Apoptosis": The Molecular Basis of Cell Death, Cold Spring Harbor Laboratory Press, p. 61, 1991). This idea however, opens a door for a new concept in cancer therapy—Cancer cells may be killed by encouraging apoptosis. Apoptosis modulation, based on the processes present in normal development, is a potential mechanism for controlling the growth of tumor cells. Restoring apoptosis in tumor cells is an attractive approach because, at least in theory, it would teach the cells to commit suicide. Nevertheless, since the objective of cancer treatment is to kill cancer cells without killing the host, although apoptosis may open a new door for cancer therapy by inducing apoptosis in tumor cells, the success of this treatment is still dependent on the availability of drugs that can selectively induce apoptosis in tumor cells without affecting normal cells. In this patent application, we described the methods for the isolation of proteins that specifically induce apoptosis in cancer cells without effect in normal cells. These proteins may present a new class of anticancer drugs that induce apoptosis in cancer cells, which may offer a breakthrough in cancer therapy.

SUMMARY OF THE INVENTION

The purpose of this invention is to characterize the specific peptide fragment derived from specially prepared zinc charged fetuin wherein the fragment was found to contain an apoptosis-inducing activity. Specifically, the amino acid sequence of this peptide is H-T-F-S-G-V-A-S-V-E (His Thr Phe Ser Gly Val Ala Ser Val Glu, SEQ ID NO:1) and correlates to amino acid no. 300–309 of fetuin, referred to herein as Fetuin Peptide Fragment (FPF 300-09). FPF 300-09 strongly induced apoptosis in LNCaP (prostate cancer) and HT-29 (colon cancer) cells without affecting CCD 18 Co (normal colon) cells. The in vitro tissue culture study demonstrated that the FPF 300-09 is more potent than the parent molecule in inducing apoptosis. FPF 300-09 has a $LD_{50}$ of 0.3–0.4 $\mu$M, while the $LD_{50}$ for zinc-charged fetuin is 3–10 $\mu$M.

DETAILED DESCRIPTION OF THE INVENTION

This patent application describes the isolation of five proteins: Apogen P-1a, Apogen 1b, Apogen 1c, Apogen P-2 and Apogen L.
(A) Isolation of Apogen P-1
(1) Source of Apogen P-1

Apogen P-1 was isolated from the conditioned medium of a cell line called XC, which was derived from rat tumor (ATCC CCL 165). XC cells were first grown in Dulbecco's Modification of Eagle's Medium (DMEM) containing 10% Fetal bovine serum (FBS) for 3 days. XC cells were then washed with PBS (3×100 ml) to remove serum and then grown in DMEM containing no FBS for 4 days. From this serum free conditioned medium, we detected an activity inducing apoptosis in a prostate cancer cell line called LNCAP. On the other hand, normal human lung fibroblast cell line (CCD 39 Lu) and breast cancer cells (MCF-7) is not affected by this activity.
(2) Activity of Apogen P-1
(a) Apoptosis Inducing Activity The activity of the crude conditioned medium of XC cells was tested on the following cell lines: JEG-3 (Choriocarcinoma), G401 (Wilm's tumor) LNCAP (Prostate cancer), T84 (colon cancer), HL-60 (leukemia), breast cancer cells (MCF-7), and CCD 39 Lu (normal lung fibroblast). When 10 folds concentrated conditioned medium was incubated for 18 hours with the above cell lines in the presence of 5% serum, the conditioned medium induced apoptosis in JEG-3 cells (35%), G 401 cell (27%), LNCaP(100%) and without activity in CCD 39 Lu (0%), T84(0%), MCF-7(0%) and HL-60(0%).

Apoptosis is a distinct type of cell death that differs fundamentally from degenerative death or necrosis in its nature and biological significance. A cell undergoing apoptosis is distinct from a cell undergoing necrosis both morphologically and biochemically. Morphologically, the earliest definitive changes in apoptosis that have been detected with the electron microscope are compaction of the nuclear chromatin into sharply circumscribed, uniformly dense masses about the nuclear envelope and condensation of the cytoplasms. Phase-contrast microscope of cells under apoptosis shows the condensation and the fragmentation of DNA and the budding of cell to form apoptotic body.

To morphologically demonstrate that the XC conditioned medium contains activity inducing apoptosis, LNCAP cells were incubated with control medium or the conditioned medium treated as described as above for 15 hr and then stained with Hoechst dye for 2 hours. The nuclei of the LNCAP cells that have been incubated with the control medium are normal and healthy. However, the nuclei of the LNCAP cells that have been incubated with the conditioned medium (X20, exchanged to RPMI) show the characteristics of apoptosis. First, the conditioned medium causes the condensation of the nucleus, demonstrated by the more intense fluorescent light compared with the control nucleus. Secondly, the nucleus condensation is accompanied by the fragmentation of DNA, demonstrated by the breakage of the nucleus. As we have mentioned above, the condensation of the nucleus and the DNA fragmentation are the morphological characteristics of cells under apoptosis. These results suggest that the conditioned medium from XC cells contain an activity inducing apoptosis in LNCAP cells. On the other hand, the conditioned medium fails to induce apoptosis in normal human lung fibroblast (CCD 39 Lu cells) and breast cancer cells (MCF-7). The nuclei of CCD 39 Lu cells remain the same with or without incubating with the conditioned medium of XC cells.
(b) Cell Repelling Activity The partially purified Apogen P-1b (Q2 anionic exchanger chromatography step) isolated as described below was recently found to contain an activity other than inducing apoptosis. We found that Apogen P-1b have the activity to repel cells away. This activity is opposite to that of growth factors; many growth factors such as Platelet Derived Growth Factor (PDGF), Epidermal Growth factor (EGF), Fibroblast Growth factor (FGF) or Transforming Growth factor (TGF) function as a "chemoattractant"—which means that these growth factors attract cells toward them. (Grotendorst, G. R. et al., Proc. Natl. Acad. Sci. 78:3669, 1981; Grant, M. B. et al Invest. Ophthal. Visual Science. 33:3292, 1992). This finding suggests that Apogen P-1b isolated in this invention plays an opposite biological function as that of a growth factor. For example, growth factors induce cell growth and attract cells, whereas Apogen P-1b induces cell death and repels cells. Apogen P-1b is the first "chemorepellent" found in the field of modern biology.

A tissue culture device called Transwell Insert purchased from Costar (Cambridge, Mass.) was used to discover the chemorepellent activity of Apogen P-1b. This device, which has been widely used for the studies of cell migration/invasion, contains an upper chamber and a lower chamber. Between these two chambers is a polyester microporous membrane with 3.0 µm pore size, which allows cells to migrate through the membrane. Tested cells are grown on the upper chamber, and the tested compound is placed in the lower chamber. If this tested compound is a chemoattractant, we should see more cells migrate through the membrane than the control sample. In our experiments, Hep G2 (100, 000 cells) cells, which have a cell size 3–4 times as big as the membrane pore size, were grown in the upper chamber for 2 hours, and then, the partially purified Apogen-1b (30 µl) isolated by ammonium sulfate precipitation and Q2 HPLC chromatography as described above was placed in the lower chamber. After 15 hours, cells that have migrated through the membrane were collected by treating the membrane with 0.2 ml of trypsin solution for 30 min. Cells in ten microliters of the trypsin solution were counted in a hemacytometer. In several experiments, we found that the partially purified Apogen-1b contained an activity decreasing the number of cells going through the membrane. For example, in one experiment, in the presence of the partially purified Apogen P-1b, the cell number in 10 microliters trypsin solution (which are the cells go through membrane) is 24+−4, whereas the number of cells that go through the membrane in the control experiment is 82+−27. This result suggests that the partially purified Apogen P-1b prevents Hep G2 cells from migrating through membrane. To unequivocally show that Apogen P-1b repel cells, an inverted experiment was installed, instead of placing Apogen P-1b in the lower chamber, we placed Apogen P-1b in the upper chamber, after for 12 hours, we found that 56+−19 cells went through membrane compared with control experiment of 30+−1.7 cells per 10 microliters of trypsin solution. The statistically significant increase or decrease in the number of cells going through the membrane by alternatively placing Apogen P-1b in the upper or lower chamber of this tissue culture device strongly suggests that Apogen P-1b repels cells.

(3) Isolation of Apogen P-1from XC Conditioned Medium

The Apogen P-1present in the conditioned medium was isolated by the following steps:

Step 1: Ammonium Sulfate Precipitation

Apogen P-1was precipitated by 80% saturated of ammonium sulfate by adding 561 g of ammonium sulfate per liter of conditioned medium. Pellet was collected by centrifugation and the proteins were dissolved in 10 mM Tris-HCl (pH 7.4). After removal of ammonium sulfate by dialysis, the dissolved proteins were separated by a Q2 HPLC column.

Step 2: O2 HPLC Chromatography

The dissolved proteins isolated by ammonium sulfate precipitation were concentrated and loaded on to a Q2 column (Bio-Rad) which was further developed by a linear gradient constructed by buffer A (10 mM Tris-HCl, pH 7.4) and buffer B (10 mM Tris-HCl, pH 7.4, 0.55 M NaCl) using BioRad's BioLogic HPLC system. The linear gradient was constructed by increasing buffer B from 0% to 100% in buffer A within 10 min (20 milliliter elution volume and thereafter the column was eluted with 100% buffer B for 5 min.

The Apogen P-1 activity was assayed by the induction of apoptosis in LNCAP cells. We found that there were three activity peaks across the chromatogram profile. Fraction 5 to 7 caused 70% cell death; fraction 8–10 caused 65% cell death; and fraction 11–14 caused 90% cell death in 18 hr. We collected fractions 5–7 and named it Apogen P-1a; fractions 8–10 was named Apogen P-1b; and fractions 11 to 14 was named Apogen P-1c. These three Apogen P-1's were further purified by a reverse phase column.

Step 3: Reverse Phase Chromatography

Apogen P-1a, Apogen P-1b and Apogen P-1c were separately concentrated to 1.5 ml. One ml of methanol containing 0.05% trifluoracetic acid was added. In each sample, a large amount of protein was precipitated by this treatment. Whereas, the apoptosis inducing activity remained in the supernatant. The supernatant was then applied to a reverse phase RP-4 column (Micra Scientific Inc) and developed by a linear gradient constructed by solution A (H20, 0.05% TFA) and solution B (Methanol, 0.05% TFA). The linear gradient was constructed by increasing solution B from 0% to 100% in solution A within 10 min (20 milliliter elution volume and thereafter the column was eluted with 100% solution B for 5 min).

Step 4: Preparative Electrophoresis

Apogen 1c isolated by anion exchange chromatography was purified by both Reverse phase chromatography (step 3) and Preparative Electrophoresis by a MiniPrep Gel electrophoresis (Bio-Rad). In the reverse phase chromatogram of Apogen P-1a, fractions 12–13 had activity inducing 80% cell death in LNCAP cells at 10 hr. In the reverse phase chromatogram of Apogen P-1b, fractions 14 and 15 had activity inducing 45% cell death in LNCAP cells at 18 hr.

In the reverse phase chromatogram of Apogen P-1c, fraction No. 5 had activity inducing 52% cell death in LNCAP cells at 18 hr.

The purity of the isolated Apogen P-1a, Apogen P-1b and Apogen P-1c was checked with SDS-polyacrylamide gel electrophoresis stained with silver staining.

(1) Apogen P-1a: a protein band with molecular weight of 70 KD was obtained. This result suggests the nearly successful purification of Apogen P-1a, which has the molecular weight of 70 KD on SDS-PAGE.

(2) Apogen P-1b: A single faint protein band with molecular weight of 55 KD was obtained. This result suggests the successful purification of Apogen P-1b, which has the molecular weight of 55 KD on SDS-PAGE.

(3) Apogen P-1c: The purification of Apogen 1c by Reverse Phase chromatography leads to the isolation of a 70 KD protein whereas the purification of Apogen-1c by preparative electrophoresis leads to the purification of a 57 KD protein. A major protein band with molecular weight of 70 KD was obtained by Reverse Phase chromatography. A 57 KD protein, on the other hand, was isolated by preparative electrophoresis.

Our next step, obviously, will be put our entire efforts on obtaining enough of the protein band for an amino acid sequence.

(B) Isolation of Apogen P-2

(1) Source of Apogen P-2

Apogen P-2 was isolated from the conditioned medium of a cell line called C3H 1OT1/2 which was derived from mouse embryo cells (ATCC CCL 226). C3H 1OT1/2 cells were first grown in alpha Modification of Eagle's Medium (alpha-MEM) containing 10% Fetal bovine serum (FBS) for 3 days. Cells were then washed with PBS (3×100 ml) to remove serum and then grown in alpha-MEM containing no FBS for 4 days. From this serum free conditioned medium, we detected an activity inducing apoptosis in a prostate cancer cell line called LNCAP. On the other hand, normal human lung fibroblast cell line (CCD 39 Lu) was not affected by this activity.

(2) Activity of Apogen P-2

(a) Apoptosis Inducing Activity

The activity of the crude conditioned medium of C3H 1OT1/2 cells was tested on the following cell lines: LNCAP (Prostate cancer), breast cancer cells (MCF-7), and CCD 39 Lu (normal lung fibroblast). When the 10-fold concentrated conditioned medium was incubated for 18 hours with the above cell lines in the presence of 5% serum, the conditioned medium induced apoptosis in LNCaP(100%) and without activity in CCD 39 Lu (0%). To morphologically demonstrate that the C3H 1OT1/2 conditioned medium contains activity inducing apoptosis, LNCAP cells were incubated with control medium or with the conditioned medium treated as described as above for 15 hr and then stained with Hoechst dye for 2 hours. The nuclei of the LNCAP cells that have been incubated with control medium are normal and healthy. However, the nuclei of the LNCAP cells that have been incubated with the conditioned medium show the characteristic of apoptosis. First, the conditioned medium causes the condensation of the nucleus, demonstrated by the more intense fluorescent light as compared with the control nucleus. Secondly, the condensation of the nucleus is accompanied by the fragmentation of DNA, demonstrated by the breakage of nucleus. As we have mentioned above, the condensation of the nucleus and DNA fragmentation are the morphological characteristics of cells under apoptosis. The same holds true of breast cancer cells (MCF-7) in which 85% apoptotic effect was observed after 18 hours of exposure to P-2. These results suggest that the conditioned medium from C3H1OT1/2 cells contains an activity inducing apoptosis in LNCAP and MCF-7 cells. On the other hand, the conditioned medium fails to induce apoptosis in normal human lung fibroblast (CCD 39 Lu cells). The nuclei of CCD 39 Lu cells remain the same with or without incubating with the conditioned medium of C3H10T1/2 cells.

(b) Cell Repelling Activity

The partially purified Apogen P-2, isolated by ammonium sulfate precipitation, hydroxylapatite, and heparin treatment as described above, was recently found to contain an activity other than inducing apoptosis. Similar to Apogen P-1b, Apogen P-2 has the activity to repel cells away. Transwell Insert purchased from Costar (Cambridge, Mass.) was used to discover the chemorepellent activity of Apogen P-2. This device, which has been widely used for the study of cell migration/invasion, contains an upper chamber and a lower chamber. Between these two chambers is a polyester microporous membrane with 3.0 $\mu$m pore size, which allows the cells to migrate through the membrane. The tested cells (HL-60) were grown on the upper chamber, and the tested compound (Apogen P-2) was placed in the lower chamber. In our experiments, HL-60 (100,000 cells) cells, which have a cell size 2–3 times as big as the membrane pore size, were grown in the upper chamber for 2 hours, and then, the partially purified Apogen P-2 (30 $\mu$l) isolated by ammonium sulfate precipitation, hydroxylapatite, and Heparin agarose as described above was placed in the lower chamber. After 6 hours, cells that have migrated through the membrane were collected from the lower chamber; the medium in lower chamber (0.6 ml) was centrifuged for 10 min; and the HL-60 cells that went through the membrane were collected and resuspended in 80 $\mu$l of PBS. The cells in ten microliters of the PBS solution were counted in a hemacytometer. In several experiments, we found that the partially purified Apogen P-2 contained an activity that decreases the number of cells going through the membrane. For example, in one experiment, in the presence of the partially purified Apogen P-2, the number of cells in 10 microliters PBS solution (which are the cells go through the membrane) is 47+−5.6, whereas the number of cells that go through the membrane in the control experiment is 213+−40. At this moment, no apoptosis was observed in HL-60 cells present in the upper chamber. This result suggests that the partially purified Apogen P-2 prevents the HL-60 cells from migrating through membrane.

(3) Isolation of Apogen P-2 from C3H1OT1/2 Conditioned Medium

The Apogen P-2 present in the conditioned medium was isolated by the following steps:

Step 1: Ammonium Sulfate Precipitation

Apogen P-2 was precipitated by ammonium sulfate (80% saturated) by adding 561 g of ammonium sulfate per liter of conditioned medium. The pellet was collected by centrifugation, and the proteins were dissolved in 10 mM Tris-HCl (pH 7.4).

Step 2: Hydroxylapatite Treatment

After removal of ammonium sulfate by dialysis in 10 mM Tris-HCl (pH 7.5), the dissolved proteins were incubated with Hydroxylapatite gel (Bio-Gel HTP gel, Bio-Rad) for 1hr. After removing HTP gel by centrifugation, the activity inducing apoptosis in LNCAP cells was found to be present in the supernatant, which was then further treated with Heparin agarose gel.

Step 3: Heparin Agarose Treatment

The supernatant from step 2 was further incubated with Heparin agarose (Sigma) for 1 Hr. After removing HTP gel by centrifugation, the activity inducing apoptosis in LNCAP cells was found to be present in the supernatant.

Step 4: Reverse Phase Chromatography

Apogen P-2 present in the supernatant of Heparin agarose in step 3 was further purified by reverse phase chromatography. Apogen P-2 was concentrated to 1 ml. One milliliter of methanol containing 0.05% Trifluoracetic acid was added. A large amount of protein was precipitated by this treatment. Whereas, the apoptosis inducing activity (P-2) remained in the supernatant. The supernatant was then applied to a reverse phase RP-4 column (Micra Scientific Inc) and developed by a linear gradient constructed by solution A (H20, 0.05% TFA) and solution B (methanol, 0.05% TFA). The linear gradient was constructed by increasing solution B from 0% to 100% in solution A in 10 min (20 milliliter elution volume) and thereafter the column was eluted with 100% solution B for 5 min.

In the reverse phase chromatogram of Apogen P-2, fractions 12–14 have activity inducing 80% cell death in LNCAP cells at 12 hr. The purity of the isolated Apogen P-2 was checked with SDS-polyacrylamide gel electrophoresis stained with silver staining, and a single protein band with molecular weight of 65 Kd was obtained.

(C) Isolation of Apogen L (1) Source of Apogen L

Apogen L was isolated from the conditioned medium of XC cell line (ATCC CCL 165). XC cells were grown in Dulbecco's Modification of Eagle's Medium (DMEM) containing 10% Fetal bovine serum (FBS) for 4 days. From this conditioned medium, we detected an activity inducing apoptosis in a leukemia cell line called HL-60. On the other hand, normal human lung fibroblast cell line (CCD 39 Lu) is not affected by this activity.

(2) Isolation of Apogen L from XC Conditioned Medium

The Apogen L present in the conditioned medium was isolated by the following steps:

Step 1: DE52 Absorption

The conditioned medium was incubated with the anion exchanger, DE 52 (Diethylaminoethyl cellulose, Whatman) for 1 hr. The incubation mixture was centrifuged and DE 52, which binds Apogen L was collected and washed with 10 mM Tris-HCl (pH 7.5) containing 0.15 M NaCl. Apogen L was then eluted from DE 52 cellulose by 10 mM Tris-HCl (pH 7.5) containing 0.5 M NaCl.

Step 2: Heparin Agarose Absorption

Apogen L isolated as described in step 1was further absorbed by Heparin agarose (Sigma) by incubating Apogen L with Heparin agarose for 1hr. Heparin agarose was collected by centrifugation and was washed with 10 mM Tris-HCl (pH 7.5). Apogen L absorbed in Heparin agarose was then eluted by 2 M NaCl.

Step 3: O2 HPLC Chromatography

Apogen L isolated as described above was concentrated and loaded onto a Q2 column (Bio Rad) which is further developed by a linear gradient constructed by buffer A (10 mM Tris-HCl, pH 7.4) and buffer B (10 mM Tris-HCl, pH 7.4, 0.5 M NaCl) using Bio-Rad's BioLogic HPLC system. The linear gradient was constructed by increasing buffer B from 0% to 100% in buffer A within 10 min. The purity of the isolated Apogen L was checked with SDS-polyacrylamide gel electrophoresis stained with silver staining. A single protein band with molecular weight of 55 Kd was obtained.

(3) Activity of Apogen L

The activity of Apogen L isolated as described above was tested on the following cell lines: HL-60 (leukemia) and CCD 39 Lu (normal lung fibroblast). To morphologically demonstrate that Apogen L contains activity inducing apoptosis, HL-60 cells were incubated with Apogen L isolated as described as above for 15 hr and then stained with Hoechst dye for 2 hours. The nuclei of the HL-60 cells that have been incubated with control medium are normal and healthy. However, the nuclei of the HL-60 cells that have been incubated with Apogen L show the characteristic of apoptosis. First, Apogen L causes the condensation of nucleus, demonstrated by the more intense fluorescent light compared with the control nucleus. Secondly, the nucleus condensation is accompanied by the fragmentation of DNA, demonstrated by the breakage of nucleus. As we have mentioned above, the nucleus condensation and DNA fragmentation are the two morphological characteristics of cells under apoptosis. These results suggest that the isolated Apogen L contains an activity inducing apoptosis in HL-60 cells. Apogen L also induces apoptosis in MCF-7 (breast cancer) cells. On the other hand, the conditioned medium fails to induce apoptosis in normal human lung fibroblast (CCD 39 Lu cells).

EXAMPLES

A. Methods

1. Preparation of Condition Media

A. Preparation of XC Condition Medium for Isolation of Apogen P-1

Apogen P-1was isolated from the conditioned medium of a cell line called XC, which was derived from a rat tumor (ATCC CCL 165). XC cells were first seeded in a roller bottle (Polystyrene, area surface=850 Cm2, Corning) in Dulbecco's Modification of Eagle's Medium (DMEM) containing CO2, 10% fetal bovine serum (FBS), non-essential amino acids, penicillin and streptomycin for 3 days. XC cells were then washed with PBS (3×100 ml) to remove serum and then grown in 100 ml of DMEM containing no FBS (with CO2), non-essential amino acids, penicillin and streptomycin) for 4 days. The conditioned medium was collected and clarified by centrifugation.

B. Preparation of C3H 10T1/2 Condition Medium for Isolation of Apogen P-2

Apogen P-2 was isolated from the conditioned medium of a cell line called C3H1OT1/2, which was derived from a mouse embryo and was purchased from American Type Culture Collection (ATCC CCL 226). C3H1OT1/2 cells were first seeded in a roller bottle (Polystyrene, area surface=850 Cm2, Corning) in alpha Modification of Eagle's Medium (alpha-MEM) containing CO2, 10% Fetal bovine serum (FBS), penicillin and streptomycin for 3 days. C3H1OT1/2 cells were then washed with PBS (3×100 ml) to remove serum and then grown in 100 ml of alpha MEM containing no FBS (with CO2, penicillin and streptomycin) for 4 days. The conditioned medium was collected and clarified by centrifugation.

C. Preparation of XC Condition Medium for Isolation of Apogen L

Apogen L was isolated from the conditioned medium of a cell line called XC, which was derived from rat tumor (ATCC CCL 165). XC cells were first seeded in a roller bottle (Polystyrene, area surface=850 Cm2, Corning) in Dulbecco's Modification of Eagle's Medium (DMEM) containing penicillin, streptomycin, CO2, non-essential amino acids and 10% Fetal bovine serum (FBS) for 4 days. The conditioned medium was collected and clarified by centrifugation.

2. Assays (a) Cell Death (Apoptosis) Assay

Prostate cancer cell line LNCAP was routinely used for the isolation of Apogen P-1and Apogen P-2, whereas leukemia cell line HL-60 was used for the isolation of Apogen L. The methods of assays were as follows: LNCAP or HL-60 (1,000 cells) was seeded in 10 microliters RPMI containing 15% or 20% Fetal bovine serum, penicillin and streptomycin at 37 degrees, 5% CO2 in Microtray plates (25 μl wells, Robbins Scientific Corp.). The tested sample (10 μl) was added 3–4 hours after cells were seeded. After incubation of the tested sample with cells for 15 hours, two microliters of Hoechst dye (0.03 ng/ml in PBS) was added. Two hours later, cells that were stained with Hoechst dye were examined under fluorescence microscope. The nuclei of apoptotic cells showed DNA condensation and fragmentation, which are easily identified by Hoechst dye staining. The percentage of apoptotic cells was calculated by the following equation:

$$\% \text{ Apoptotic cells} = \frac{\text{Number of cells with DNA condensation and fragmentation}}{\text{Total cell number}}$$

(b) Cell Repelling Assay

There are two reasons that Hep G2 cells are chosen for the study of cell repelling activity. First, Hep G2 cells are not sensitive to Apogen P-1 in inducing apoptosis. Secondly, the cell size of Hep G2 cell is about 3–4 times as big as the pore size of the membrane on the Transwell Insert, which is a good cell size for cell migration/invasion study. A tissue culture device called Transwell Insert purchased from Costar (Cambridge, Mass.) was used to discover the chemorepellent activity of Apogen P-1b. This device, which has been widely used for the studies of cell migration/invasion, contains an upper chamber and a lower chamber. Between these two chambers is a polyester microporous membrane with 3.0 μm pore size, which allows cells to migrate through the membrane. Tested cells were grown on the upper chamber, and the tested compound was placed in the lower chamber. If this tested compound is a chemoattractant, we should see more cells migrate through membrane than the control sample. In our experiments, Hep G2 (100,000 cells) cells, which have a cell size 3–4 times as big as the membrane pore size were grown in the upper chamber (Minimum Essential Medium Eagle containing 10% FBS, PS and nonessential amino acid, 0.1 ml) for 2 hours, and then the partially purified Apogen-1b (30 μl) isolated by ammonium sulfate precipitation and Q2 HPLC chromatography as described above was placed in the lower chamber which contains 0.6 ml of the same growth medium for Hep G2 cells. After 15 hours, cells that have migrated through the membrane were collected by treating the membrane with 0.2 ml of trypsin solution for 30 min. Cells in ten microliters of the trypsin solution were counted in a hemacytometer.

3. Protein Isolation

A. Isolation of Apogen P-1

Step 1: Ammonium Sulfate Precipitation

Apogen P-1was precipitated by 80% saturated of ammonium sulfate by adding 561 g of ammonium sulfate per liter of XC conditioned medium. The pellet was collected by centrifugation, and the proteins were dissolved in 10 mM Tris-HCl (pH 7.4). After removal of ammonium sulfate by dialysis, the dissolved proteins were separated by a Q2 HPLC column.

Step 2: O2 HPLC Chromatography

The dissolved proteins isolated by ammonium sulfate precipitation were concentrated and loaded onto a Q2 column (Bio Rad) which was further developed by a linear gradient constructed by buffer A (10 mM Tris-HCl, pH 7.4) and buffer B (10 mM Tris-HCl, pH 7.4, 0.55 M NaCl) using BioRad's BioLogic HPLC system. The linear gradient was constructed by increasing buffer B from 0% to 100% in buffer A within 10 min (20 milliliter elution volume) and thereafter the column was eluted with 100% buffer B for 5 min. The Apogen P-1 activity was assayed by the induction of apoptosis in LNCAP cells. We found that there are three activity peaks across the chromatogram profile. Fractions 5 to 7 cause 70% cell death; fractions 8–10 cause 65% cell death; and fractions 11–14 caused 90% cell death in 18 hr. We collected fractions 5–7 and named it Apogen P-1a; fractions 8–10 was named Apogen P-1b; and fractions 11–14 was named Apogen P-1c. These three Apogen P-1's were further purified by a reverse phase column.

Step 3: Reverse Phase Chromatography

Apogen P-1a, Apogen P-1b and Apogen P-1c were separately concentrated to 1.5 ml. One ml of methanol containing 0.05% Trifluoracetic acid was added. In each sample, a large amount of protein was precipitated by this treatment. Whereas, the apoptosis inducing activity remained in the supernatant. The supernatant was then applied to a reverse phase RP-4 column (Micra Scientific Inc) and developed by a linear gradient constructed by solution A (H20, 0.05% TFA) and solution B Methanol, 0.05% TFA). The linear gradient was constructed by increasing solution B from 0% to 100% in solution A within 10 min., 20 milliliter elution volume, and thereafter the column was eluted with 100% solution B for 5 min.

Step 4: Preparative Electrophoresis

Apogen 1c isolated by anion exchange chromatography was purified by both Reverse Phase Chromatography (step 3) and Preparative Electrophoresis by a MiniPrep Gel electrophoresis (Bio-Rad). In the reverse phase chromatogram of Apogen P-1a, fractions 12–13 have activity inducing 80% cell death in LNCAP cells at 10 hr.

In the reverse phase chromatogram of Apogen P-1b, fractions 14 and 15 have activity inducing 45% cell death in LNCAP cells at 18 hr.

In the reverse phase chromatogram of Apogen P-1c, fraction No. 5 has activity inducing 52% cell death in LNCAP cells at 18 hr.

The purity of the isolated Apogen P-1a, Apogen P-1b and Apogen P-1c were checked with SDS-polyacrylamide gel electrophoresis stained with silver staining.

(1) Apogen P-1a: A protein band with molecular weight of 70 KD was obtained. This result suggests the nearly successful purification of Apogen P-1a, which has a molecular weight of 70 KD on SDS-PAGE.

(2) Apogen P-1b: A single faint protein band with molecular weight of 55 KD was obtained. This result suggests the successful purification of Apogen P-1b, which has a molecular weight of 55 KD on SDS-PAGE.

(3) Apogen P-1c: The purification of Apogen 1c by Reverse Phase chromatography leads to the Isolation of a 70 KD protein, whereas the purification of Apogen 1c by preparative electrophoresis leads to the purification of a 57 KD protein. A major protein band with molecular weight of 70 KD was obtained by Reverse Phase chromatography. A 57 KD protein, on the other hand, was isolated by preparative electrophoresis.

B. Isolation of Apogen P-2

The Apogen P-2 present in C3H10T1/2 conditioned medium was isolated by the following steps:

Step 1: Ammonium Sulfate Precipitation

Apogen P-2 was precipitated by ammonium sulfate (80% saturated) by adding 561 g of ammonium sulfate per liter of conditioned medium. The pellet was collected by centrifugation, and the proteins were dissolved in 10 mM Tris-HCl (pH 7.4).

Step 2: Hydroxylapatite Treatment

After removal of ammonium sulfate by dialysis in 10 mM Tris-HCl (pH 7.5), the dissolved proteins were incubated with hydroxylapatite gel (Bio-Gel HTP gel, Bio-Rad) for 1 hr. After removing HTP gel by centrifugation, the activity inducing apoptosis in LNCAP cells was found to be present in the supernatant, which was then further treated with Heparin agarose gel.

Step 3: Heparin Agarose Treatment

The supernatant from step 2 was further incubated with Heparin agarose (Sigma) for 1 hr. After removing HTP gel by centrifugation, the activity inducing apoptosis in LNCAP cells was found to be present in the supernatant.

Step 4: Reverse Phase Chromatography

Apogen P-2 presents in the supernatant of Heparin agarose in step 3 was further purified by reverse phase chromatography. Apogen P-2 was concentrated to 1 ml. One milliliter of methanol containing 0.05% trifluoacetic acid was added. Large amounts of proteins were precipitated by this treatment. Whereas, the apoptosis inducing activity (P-2) remained in the supernatant. The supernatant was then applied to a reverse phase RP-4 column (micra Scientific Inc.) and developed by a linear gradient constructed by solution A (H20, 0.05% TFA) and solution B Methanol (0.05% TFA). The linear gradient was constructed by increasing solution B from 0% to 100% in solution A within 10 min (20 milliliter elution volume) and thereafter the column was eluted with 100% solution B for 5 min. In the reverse phase chromatogram of Apogen P-2, fractions 12–14 have activity inducing 80% cell death in LNCAP cells at 12 hr. The purity of the isolated Apogen P-2 was checked with SDS-polyacrylamide gel electrophoresis stained with silver staining. A single protein band with molecular weight of 65 Kd was obtained.

C. Isolation of Apogen L

The Apogen L present in the conditioned medium was isolated by the following steps:

Step 1: DE52 Absorption

The conditioned medium was incubated with the anion exchanger, DE 52 (Diethylaminoethyl cellulose, Whatman) for 1 hr. The incubation mixture was centrifuged, and DE 5 2, which binds Apogen L, was collected and washed with 10 mM Tris-HCl (pH 7.5) containing 0.15 M NaCl. Apogen L was then eluted from DE 5 2 cellulose by 10 mM Tris-HCl (pH 7.5) containing 0.5 M NaCl.

Step 2: Heparin Agarose Absorption

Apogen L isolated as described in step 1 was further absorbed by Heparin agarose (Sigma) by incubating Apogen L with Heparin agarose for 1 hr. Heparin agarose was collected by centrifugation and was washed with 10 mM Tris-HCl (pH 7.5). Apogen L absorbed in Heparin agarose was then eluted by 2 M NaCl.

Step 3: O2 HPLC Chromatography

Apogen L isolated as described above was concentrated and loaded onto a Q2 column (Bio Rad) which was further developed by a linear gradient constructed by buffer A (10 mM Tris-HCl, pH 7.4) and buffer B (10 mM 22 Tris-HCl, pH 7.4, 0.5 M NaCl) using Bio-Rad's BioLogic HPLC system. The linear gradient was constructed by increasing buffer B from 0% to 100% in buffer A in 10 min. The purity of the isolated Apogen L was checked with SDS-polyacrylamide gel electrophoresis stained with silver staining. A single protein band having activity with a molecular weight of approximately 55 Kd was obtained.

4. Isolation of Bovine Fetuin as a Component of Protein P-2 and the Apoptotic Effect Thereof in Tumor Cell Lines The observation that Apogen P-1a, P-1b, P-1c, P-2 and L were isolated from embryonic cell lines led us to speculate that newborn or embryonic tissue may secrete "Apogen," which may selectively induce apoptosis in tumor cell lines.

Thus, due to this speculation, a protein named "Fetuin" has raised our attention for the following reasons: (1) Fetuin is mainly a fetal protein, in the sense that the highest concentrations are found in serum and body fluids of embryos and fetuses. For example, the concentration of fetuin in bovine serum drastically decreases, probably within a few days after birth, to 1–2% of the fetal level. (Yang, et al., Biochim. Biophy. Acta. 1130, 149–156 1992). (2) A histochemical study has shown that fetuin may control tissue remodelling and physiological cell death during embryonic development. (Von Bulow, et al., Histochemistry 99:13–22, 1993). This result raises the possibility that fetuin may contain activity inducing cell death (apoptosis).

Additionally, a protein with an amino acid sequence identical to Fetuin was isolated from the preparation of Apogen P-2. Thus, the composition of Apogen P-2 consists at least in part of fetuin.

We therefore prepare and obtain fetuin and test fetuin in our apoptosis assay. Interestingly, we found that only bovine fetuin that is prepared by a special method is able to induce apoptosis in tumor cell lines. The commercial fetuin that is prepared by ammonium sulfate precipitation and EDTA treatment was found to contain a very low activity in inducing apoptosis in tumor cells.

4A. Preparation of Bovine Fetuin

Bovine fetuin was prepared by the modified Spiro method (Spiro R. G., Journal of Biological Chemistry 235, 10: 2860, 1960) according to the following steps:

1. One hundred milliliters of Fetal Bovine Serum (FBS).
2. Add two hundred milliliters of 0.05 M Zinc Acetate containing 30% (V/V) ethanol, adjust to pH 6.4 by 1M NH4OH—NH4Cl, let stand 15 hours at −5° C.
3. Collect the supernatant by centrifugation, add 1.0 M Barium Acetate and 95% ethanol to give 0.03 M Barium Acetate, 25% ethanol. Let stand 2 hours at −5° C.
4. Collect the supernatant by centrifugation, add 95% ethanol to give 40% ethanol. Let stand 15 hours at −10° C.
5. Collect the precipitate. Dissolve the pellet by phosphate buffer saline.

The purified fetuin showed a single protein band with apparent molecular weight of 63 Kd on SDS-PAGE.

4B. Induction of Apoptosis in Tumor Cell Lines Using Bovine Fetuin

Fetuin purified from fetal bovine serum by the procedure described above was dissolved in phosphate buffer saline (PBS). The free Zinc Acetate and Barium Acetate were removed by repetitive concentration. Fetuin was tested in LNCaP and HL-60 cells. LNCaP or HL-60 (1,000 cells) was seeded 10 microliters RPMI containing 15% or 20% Fetal bovine serum, penicillin and streptomycin at 37 degree, 5% CO2 in microtray plates (25 μl wells, Robbins Scientific Corp.). Fetuin (in 10 μl PBS) at concentration of 100 ng/ml was added 3–4 hours after cells were seeded. After incubation of the tested sample with cells for 15 hours, two microliters of Hoechst dye (0.03 ng/ml in PBS) was added. Two hours later, cells that were stained with Hoechst dye were examined under fluorescence microscope. The nuclei of apoptotic cells showed DNA condensation and fragmentation, which can be easily identified by Hoechst dye staining. The percentage of apoptotic cells was calculated by the following equation:

$$\% \text{ Apoptotic cells} = \frac{\text{Number of cells with DNA condensation and fragmentation}}{\text{Total cell number}}$$

The nuclei of the LNCaP cells that have been incubated with control sample (PBS) are normal and healthy. However, the nuclei of the LNCaP cells that have been incubated with fetuin (100 ng/ml in PBS) show the characteristics of apoptosis. First, the cells in the presence of fetuin showed the condensation of nucleus, demonstrated by the more intense fluorescent light compared with the control nucleus. Secondly, the nucleus condensation is accompanied by the fragmentation of DNA, demonstrated by the breakage of nucleus. As the condensation of the nucleus and the DNA fragmentation are the two morphological characteristics of cells under apoptosis. These results suggest that fetuin contains an activity inducing apoptosis in LNCaP cells. The nuclei of the HL-60 cells that have been incubated with control buffer (PBS) are normal and healthy. However, the nuclei of the HL-60 cells that have been incubated with fetuin show the characteristics of apoptosis. Fetuin causes the condensation of nucleus, demonstrated by the more intense fluorescent light compared with the control nucleus. Secondly, the nucleus condensation is accompanied by the fragmentation of DNA, demonstrated by the breakage of the nucleus. As we have mentioned above, the nucleus condensation and DNA fragmentation are the two morphological characteristics of cells under apoptosis. These results suggest that fetuin contains an activity inducing apoptosis in HL-60 cells.

4C. Bovine Fetuin Selectively Induces Apoptosis in Cancer Cells without Having an Effect on Normal Cell Lines We compared the effect of fetuin on the induction of apoptosis in various cell lines. At a concentration of 50 μg/ml, fetuin prepared as described above strongly induced apoptosis in tumor cell lines such as: LNCaP (prostate cancer), PC-3 (prostate cancer), HL-60 (leukemia), MCF-7 (breast cancer), Colo 205 (colon cancer), Calu-1 (lung cancer). Normal lung fibroblast (CCD 39 Lu), on the other hand, is not affected by fetuin.

Fetuin was found to be inactive in inducing apoptosis in CCD 39 Lu cells (normal lung fibroblast) at the concentration (25 μg/ml) that highly induced apoptosis in LNCaP (prostate cancer) or HL-60 cells (leukemia). Fetuin (25 μg/ml) prepared as described above was incubated with CCD 39 Lu cells grown in MEM in a microtray plate for 15 hours. The CCD 39 Lu cells remained morphologically unchanged in the presence of fetuin. At this concentration (25 μg/ml) of fetuin and in the presence of fetuin, less MCF-7 cells remaining, due to cell death and cell shrinkage, was observed.

4D. Only Fetuin Prepared by the Method Described above is Able to Induce Apoptosis in Tumor Cell Lines We found that fetuin purchased from Sigma has a very low activity in inducing apoptosis in LNCaP cells. However, fetuin (25 μg/ml) prepared in our laboratory by the method described in Section 4A above induces apoptosis in LNCaP cells by up to 90% in 4 hours. For the fetuin purchased from Sigma, apoptosis inducing activity was observed only at a very high concentration (>250 μg/ml) and at long incubation time (2 days). We estimated that the activity of fetuin prepared in our laboratory is more than fifty thousand folds higher than that of fetuin prepared by other methods.

In the years of research following the original findings, I have observed that fetuin from Sigma induces apoptosis at a very high concentration and at a long incubation time (2 days). It is conservatively estimated that the fetuin as prepared in Section 4A has more than one hundred times greater apoptotic activity than fetuin prepared by other methods. While this is not as dramatic as the 50,000 times increase as originally reported, it still represents a significant apoptotic advantage over previously available fetuin in terms of incubation time and $LD_{50}$ values.

We have examined the preparation method for Sigma's fetuin and found that these fetuins are prepared by methods including ammonium sulfate precipitation and EDTA treatment. Both treatments may cause the deprivation of the Zinc ion from the protein, which may cause the irreversible loss of the protein activity.

4E. Effect of Fetal Fetuin on Leukemia Cells in vivo

Figure 1:
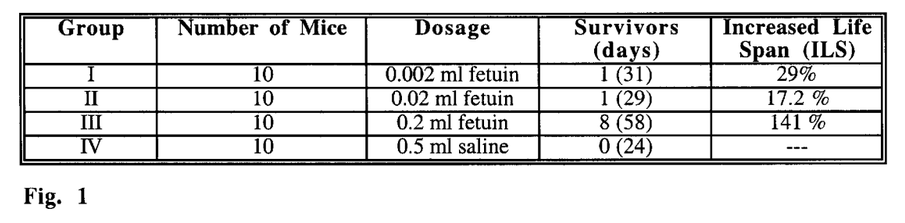
FIG. 1 shows a table of test data of using fetal fetuin on mice bearing leukemia.

Our previous data demonstrated that fetuin induced apoptosis in cancer cells in vitro. The data provided below shows that the in vivo testing of fetuin in mice having leukemia was successful. The results show that fetuin has an anti-leukemia effect in mice. FIG. 1 shows the increase in survival of leukemia-bearing mice treated with fetal fetuin.

Method

Forty DBA/2 female mice (17–20 grams; Simonsen Laboratories, Inc., Gilroy, Calif.) kept on a standard diet and water ad libitum were inoculated with tumor cell line P388D1 (ATCC cell line number CCL46). The mice were randomly segregated into groups of ten (10). Zinc-charged fetal fetuin (10 mg/ml) were intraperitoneally injected into group I at 0.002 ml/mouse, group II at 0.02 ml/mouse and group III at 0.2 ml/mouse. Group IV was the control group, which was injected with 0.5 ml of saline solution. The injections were continued for 10 days. Mortalities were recorded for 60 days. The results were expressed as the percentage increase in life span (ILS):

$$ILS = \frac{100 \times \text{Median Life Span Treated} - \text{Median Life Span Controlled}}{\text{Life Span Controlled}}$$

FIG. 1 shows that while 100% of the untreated leukemia-bearing mice were dead after 24 days, 80% of the mice treated with a high dose of fetuin, namely 100 mg/Kg of fetal fetuin, survived more than 58 days. This in vivo experiment demonstrates that mice bearing leukemia that are treated with fetal fetuin have an increased life span of 141%.

4F. Method of Preparing Supercharged Zinc Fetuin

The method to prepare fetuin with zinc has been refined and improved. As stated above, fetuin prepared by the method as described in Section 4A above is able to induce apoptosis in tumor cell lines. However, commercial fetuin such as from Sigma is found to have a very low activity in inducing apoptosis in tumor cells and in inducing apoptosis in LNCaP cells. For fetuin from Sigma, apoptosis inducing activity was observed only at a very high concentration (>250 µg/ml) and at a long incubation time (2 days), whereas fetuin (25 µg/ml) as prepared in Section 4A above induced apoptosis in LNCaP cells by up to 90% in 4 hours. It was estimated that the fetuin as prepared as described in Section 4A is more than fifty thousand times higher than that fetuin prepared by other methods. The radically different results suggest a fundamental difference in the chemical composition of commercially available fetuin and the fetuin prepared in accordance with the procedure in Section 4A.

In the years of research following the original findings, I have observed that fetuin from Sigma induces apoptosis at a very high concentration (>>5 mM) and at a long incubation time (2 days), whereas fetuin (approximately 50 µM) as prepared in Section 4A above induced apoptosis in LNCaP cells by up to 90% in 4 hours. It is conservatively estimated that the fetuin as prepared in Section 4A has more than one hundred times greater apoptotic activity than fetuin prepared by other methods. While this is not as dramatic as the 50,000 times increase as originally reported, it still represents a significant apoptotic advantage over previously available fetuin in terms of incubation time and $LD_{50}$ values.

Figure 2:
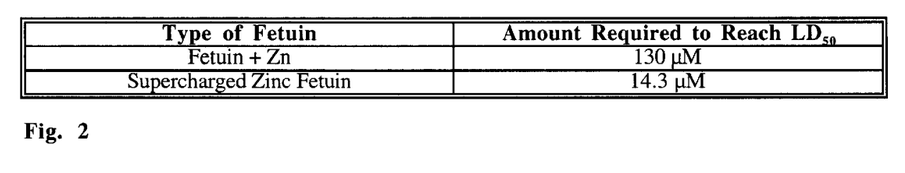
FIG. 2 shows a table of the comparison of original fetuin with zinc in comparison with the supercharged zinc fetuin to reach $LD_{50}$.
Figure 3:
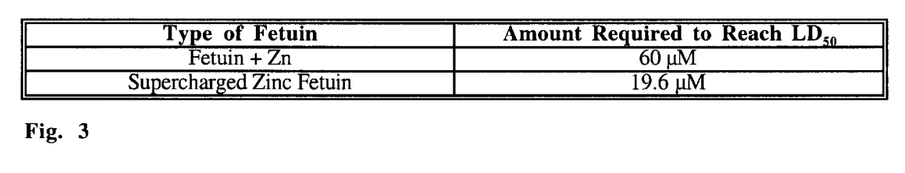
FIG. 3 shows another table of the comparison of original fetuin with zinc in comparison with the supercharged zinc fetuin to reach $LD_{50}$.

After looking at the methods of preparing commercially available fetuin, it was found that ammonium sulfate precipitation and EDTA treatment was used in preparing fetuin. It was speculated that this ammonium sulfate precipitation and EDTA treatment might cause the deprivation of the ions from the protein to cause irreversible loss of the protein activity. However, it was not known whether it was the loss of zinc alone, or in combination with the loss of another ion(s), that caused the decreased apoptotic activity in commercially available fetuin. While it was determined that Fetuin-Ca is inactive in inducing apoptosis (data not shown), and barium occurs in only trace amounts, to determine which ion, or combination of ions, were most go effective in increasing the apoptotic ability of fetuin, fetuin as prepared in Section 4A above was treated with a chelating agent, such as EDTA, to strip all the inorganic ions, including zinc, calcium, and barium from the protein. After removing these inorganic ions, the "naked" fetuin was treated or incubated with 0.5 M Zinc Acetate to reload or to bind the fetuin with zinc only. The results of this refinement process are shown in examples in FIGS. 2–3 in determining the $LD_{50}$ value. FIGS. 2–3 show that the improved preparation of Fetuin-Zn or "supercharged zinc fetuin" enhances fetuin's ability to induce apoptosis in cancer cells by three to four times as compared with the original fetuin bound with zinc as prepared in Part 4A. It is hypothesized that the fetuin previously bound up with calcium and barium created an inactive form of the protein. By stripping out all ions and replacing them with zinc, inactive fetuin molecules were converted to active form, thereby explaining the dramatic increase in apoptotic activity. Such supercharged zinc fetuin is a valuable step forward in the fight against cancer.

In one preferred embodiment of this preparation process:

1. Incubation Mixture: 700 µg of fetuin (0.2 ml; as prepared by the method as described above in Section 4A) was incubated with 0.5 ml of 0.1 EDTA for approximately one (1) hour.
2. Concentration: Add 1.5 ml of saline solution to this incubation mixture and concentrate to near dryness using a molecular or molecule sieve and centrifugal force. Repeat this procedure four (4) times, so that most of the inorganic ions are removed. This "naked" fetuin will be retained on the top of the filter (molecular sieve).
3. Incubate the "naked" fetuin (0.2 ml) with 0.5 ml of 0.5 M Zinc Acetate for approximately three (3) hours.
4. Remove the free Zinc Acetate using the combination of the saline solution, the molecular sieve, and centrifugal force as described in Step 2 above.

5. A Specific Peptide Fragment from Fetuin-zinc that causes Apoptosis in Cancer Cells a. Preparation of Fetuin Fragment As described above in Section 4F (Method of Preparing Supercharged Zinc Fetuin), zinc charged fetuin or supercharged zinc fetuin was prepared by pre-treatment of fetal bovine fetuin with a chelating agent (EDTA) to remove the inorganic ions, including zinc, calcium, and barium ions, from the fetuin. The resulting stripped fetuin was incubated with 0.5 M Zinc Acetate in order to "supercharge" or load the fetuin with zinc. Three hundred (300) micrograms of the zinc charged fetuin was dissolved in a 50 µl saline solution and then dried in a tube under a vacuum. It is hypothesized that this drying step breaks apart the zinc charged fetuin into peptide fragments.

Figure 4:
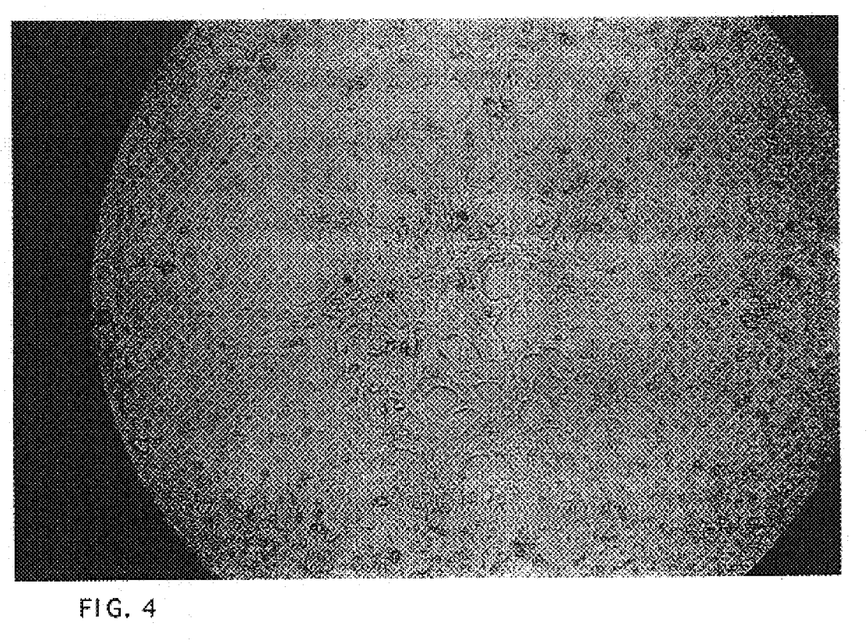
FIG. 4 shows a slide of LNCaP (prostate cancer) cells without treatment of filtrate containing FPF 300-09.
Figure 5:
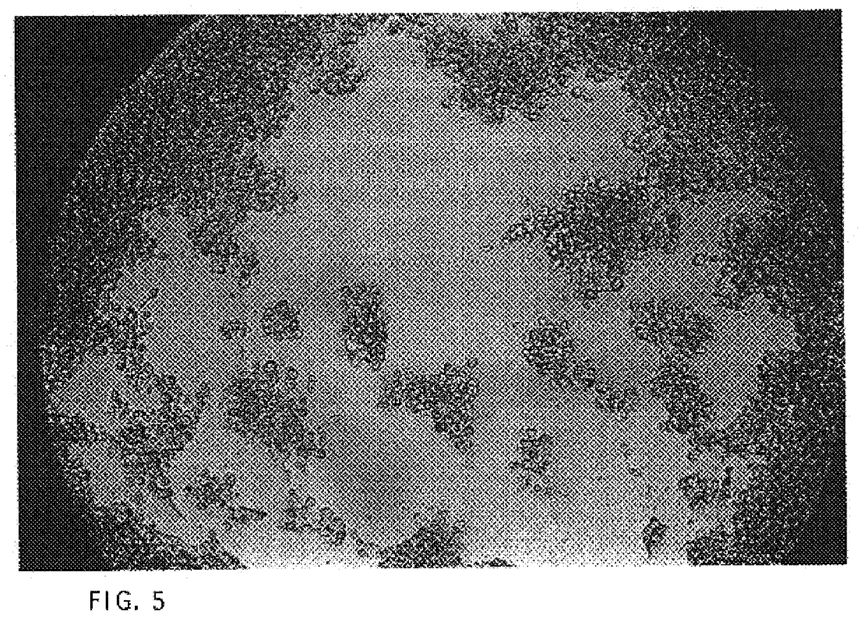
FIG. 5 shows a slide of LNCaP cells incubated with filtrate containing FPF 300-09 for six (6) hours.
Figure 6:
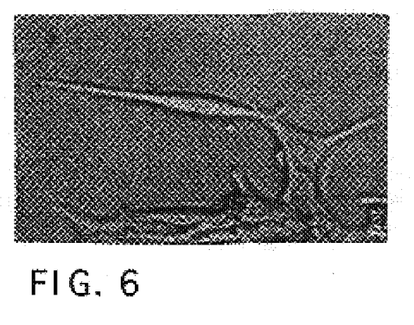
FIG. 6 shows an additional slide of LNCaP (prostate cancer) cells without treatment of filtrate containing FPF 300-09.
Figure 7:
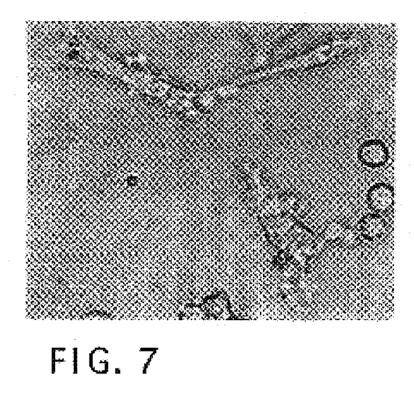
FIG. 7 shows a slide of LNCaP cells incubated with filtrate containing FPF 300-09 and which expressed membrane bubbling, which is an indicator of cells undergoing apoptosis.

The dried fragments (of zinc charged fetuin) of were reconstituted in 50 µl water. This fragment solution was passed through a molecular sieve membrane having a molecular weight cut-off of 10,000 daltons. The resulting filtrate of fragments was collected and tested on cells in an apoptosis assay. As shown in FIG. 5, when LNCaP cells are incubated with the zinc charged fetuin fragment filtrate for six (6) hours, the LNCaP cells detach and die. Compared with the control (LNCaP with no filtrate) as shown in FIG. 4, FIG. 5 shows that incubation of the prostate cancer cells with the zinc charged fetuin filtrate causes apoptosis of the cancer cells. FIG. 7 shows that the zinc charged fetuin filtrate treated LNCaP cells also exhibit membrane "bubbling," which is a characteristic typical of cells undergoing apoptosis. FIG. 6, which shows LNCaP cells without the zinc charged fetuin filtrate, lacks this membrane "bubbling" and characteristic of apoptosis.

b. Is Protease Sensitive

Additionally, the apoptosis-inducing activity of FPF 300-09 was found to be protease sensitive. Incubation of the FPF 300-09 filtrate with proteinase K completely removed the apoptosis-inducing activity. Proteinase K is an enzyme that cleaves peptide bonds; chelating agents such as citrate and EDTA have no effect on the enzyme activity of proteinase K.

After preparing "supercharged" zinc fetuin or zinc charged fetuin as stated in Section 4F above, the resulting composition was dried in a tube and under a vacuum. This dried supercharged zinc fetuin was reconstituted in 50 µl of water. This solution was filtered through a molecular sieve membrane (Centricon 10 tube with a molecular weight cut-off: 10,000 daltons). The filtrate was collected and treated with 5 µl (1unit/µl) proteinase K for three (3) hours at 37° C. After treatment with proteinase K, the treated filtrate was filtered through a molecular sieve membrane (Centricon 10 tube) in order to remove the proteinase K. The proteinase K was retained by the membrane, and the treated filtrate passed through the membrane.

To test the effect of a protease on the apoptotic activity of the filtrate, the filtrate treated with proteinase K was tested on cancer cells. These results were compared to the filtrate that was not treated with proteinase K.

Figure 8:
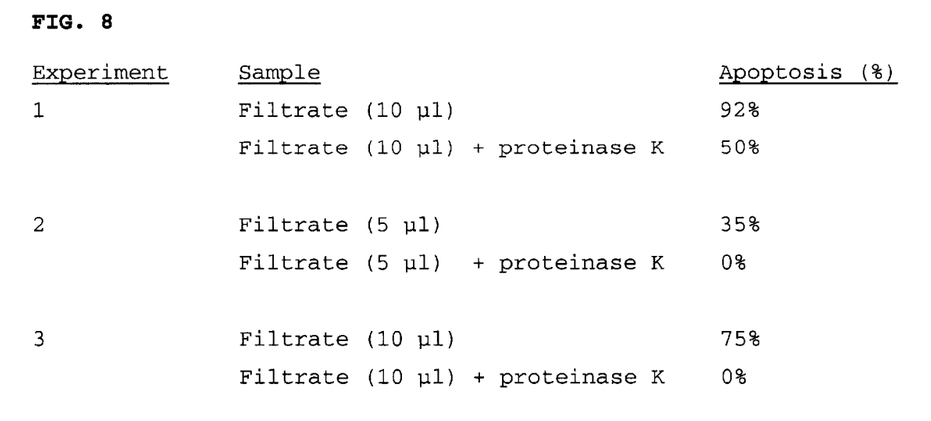
FIG. 8 shows a table illustrating, among other things, the effect of incubating the filtrate containing FPF 300-09 treated with proteinase K.

The effect of proteinase K on the apoptotic ability of the Fetuin-Zinc fragments is summarized in FIG. 8. Experiments 1and 2 were conducted with one set of zinc charged fetuin filtrate, and Experiment 3 was conducted with another set of zinc charged fetuin filtrate. FIG. 8 shows that incubation with a protease seems to inactivate the apoptotic effect of the zinc charged fetuin fragment. Because a protease, such as proteinase K, cleaves peptide bonds, the test results of FIG. 8 strongly suggest that a peptide or a protein of fetuin is responsible for the induction of apoptosis in cancer cells.

c. The Filtrate Contains Two Major Peptides Derived from Fetuin

The dried and reconstituted filtrate was found to contain peptide fragments. The amino acid sequence analysis revealed two major peptide fragments in the filtrate:

(1) H-T-F-S-G-V-A-S-V-E (amino acid no. 300–309; His Thr Phe Ser Gly Val Ala Ser Val Glu; SEQ ID NO:1) and (2) S-A-S-G-E-A-F-H (amino acid no. 310–317; Ser Ala Ser Gly Glu Ala Phe His; SEQ ID NO:2) of fetuin.

Figure 9:
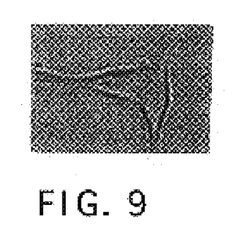
FIG. 9 shows a slide of LNCaP cells without filtrate containing FPF 300-09.
Figure 10:
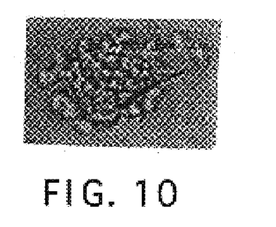
FIG. 10 shows a slide of LNCaP cells, which were incubated with filtrate containing FPF 300-09 for three (3) hours and expressed membrane "bubbling," which is an indicator of cells undergoing apoptosis.

To identify which of these peptide fragments are responsible for the apoptosis-inducing activity, the two fragments (H-T-F-S-G-V-A-S-V-E (amino acid no. 300–309; referred to herein as Fetuin Peptide Fragment (FPF 300-09); SEQ ID NO:1) and S-A-S-G-E-A-F-H (amino acid no. 310–317; SEQ ID NO:2) of the full-length fetuin molecule) were chemically synthesized. Upon in vitro testing of these chemically synthesized peptide fragments, FPF 300-09 was shown to have the greater apoptotic activity. LNCaP (prostate cancer cells) were incubated with FPF 300-09. In FIG. 10, chemically synthesized FPF 300-09 caused membrane "bubbling" in LNCaP cells after three (3) hours of incubation. Incubation of the peptide fragment (amino acid no. 310–317) or the peptide fragment (amino acid no. 300–307) with LNCaP cells did not show any apoptotic activity or membrane "bubbling." FIG. 9 shows the control of LNCaP cells without FPF 300-09. These results suggest that the peptide fragment that induced apoptosis and that was present in the filtrate corresponds to amino acid no. 300–309 of the full-length fetuin.

Figure 11:
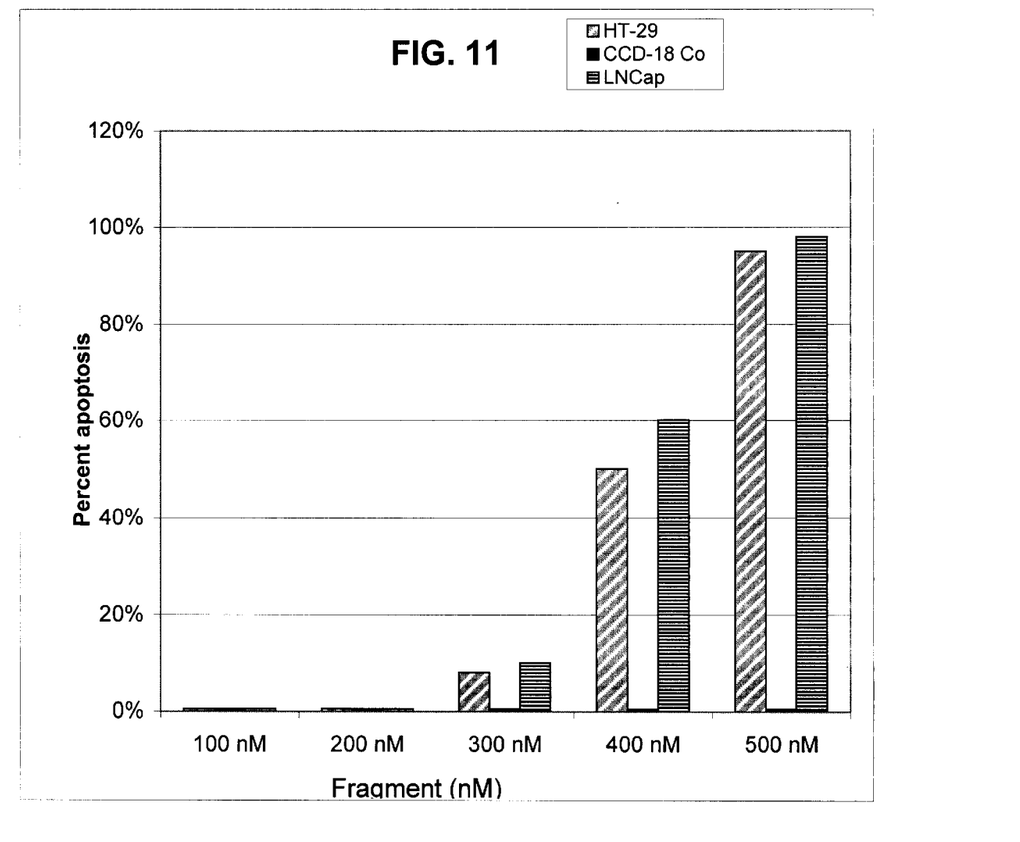
FIG. 11 is a graph of FPF 300-09 (nM) versus the percent apoptosis in HT-29, CCD-18 Co, and LNCaP cells.

6. Characterization of FPF 300-09 a. FPF 300-09 Selectively Induced Apoptosis in Cancer Cells but not in Normal Cells Previously, it was found that fetuin and zinc charged fetuin induced apoptosis in various cancer cells without affecting certain normal cells. To test whether FPF 300-09 derived from fetuin retains this selectivity in inducing apoptosis in cancer cells only and not affecting normal cells, various concentrations of FPF 300-09 were tested on HT-29 (colon cancer), CCD-18 Co (normal colon), and LNCaP (prostate cancer) cells. As shown in FIG. 11, FPF 300-09 induced apoptosis in HT-29 and LNCaP cells without affecting CCD-18 Co cells. These results suggest that the fragment was similar to fetuin and zinc charged fetuin in selectively inducing apoptosis in cancer cells and not in normal cells.

b. FPF 300-09 Rapidly Induced Apoptosis in HT-29 (Colon Cancer) Cells

Figure 12:
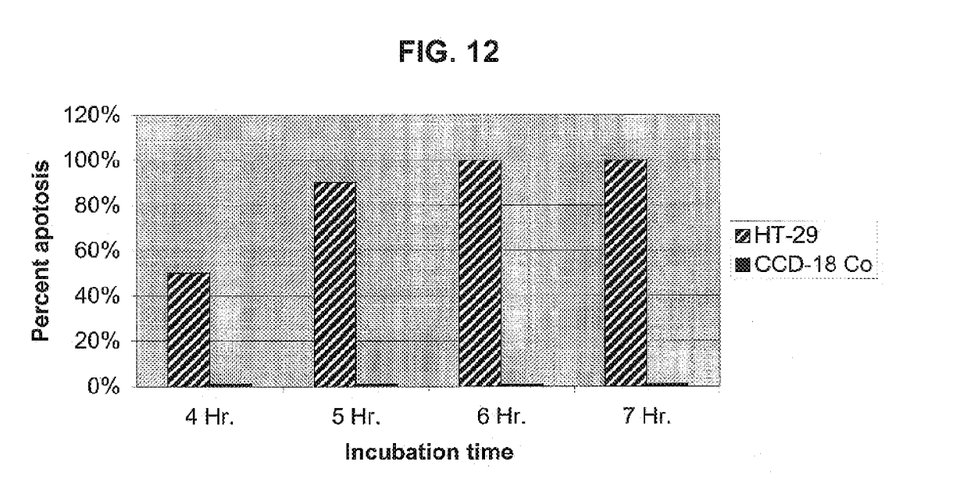
FIG. 12 is a graph of the time of incubation of FPF 300-09 filtrate versus percent apoptosis in HT-29 and CCD-18 Co cells.
Figure 13:
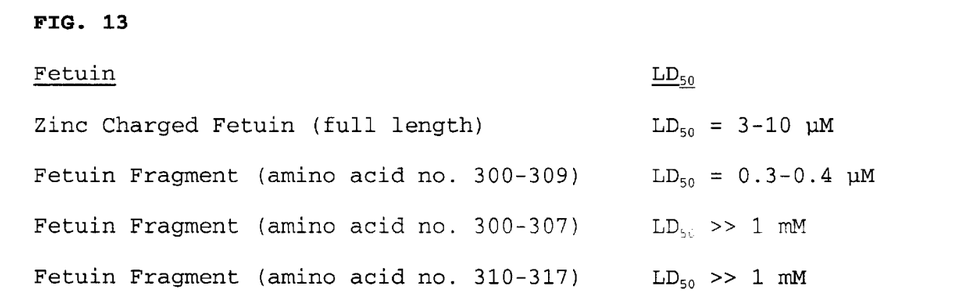
FIG. 13 is a table of the $LD_{50}$ values for fetuin and various fetuin fragments, including FPF 300-09.

FIG. 12 shows the effect of time on the induction of apoptosis by FPF 300-09. At four (4) hours, FPF 300-09 at a concentration of 0.4 µM induced apoptosis in 52% of the HT-29 colon cancer cells. At six (6) hours, almost all of the HT-29 cells were induced to apoptosis. Even with a little more incubation time (from 4 to 6 hours), the apoptotic ability of FPF 300-09 rapidly increases within this short period of time.

c. The Peptide Fragment Derived from Fetuin is more Potent than Fetuin or Zinc Charged Fetuin in Inducing Apoptosis Previously, the $LD_{50}$ (dosage for the induction of 50% cell death) for full-length zinc charged fetuin in LNCaP cells was determined to be 3–10 µM. However, the $LD_{50}$ for FPF 300-09 was determined to be 0.3–0.4 µM. Hence, with a much smaller $LD_{50}$ value, a much smaller amount of the FPF 300-09 was required to induce the same amount of cancer cells than is required with full-length zinc charged fetuin. Further, FPF 300-09 is more potent in inducing apoptosis than its parent molecule (FIG. 13).

Taking into consideration the previous estimates:

(1) Fetuin as prepared in Section 4A above is approximately 100 times more powerful than fetuin prepared from other methods;

(2) "Supercharged" Zinc Fetuin (zinc charged fetuin) is approximately three to four times more powerful than the fetuin as prepared in Section 4A (see FIGS. 2–3); and (3) FPF 300-09 is approximately eight to ten times more powerful than "Supercharged" Zinc Fetuin (see FIG.

13), it is estimated that FPF 300-09 is approximately several thousand times more powerful than fetuin prepared from other methods.

7. Other Sequences of Fetuin from other Sources

In addition, peptide sequences were determined from other animal sera, including pig, sheep and mice. K. M. Dziegielewska, et. al., *Fetuin*, 16–17, (R. G. Landes Co. 1995). These peptide sequences have a similarity of 60–90% with the fetuin isolated from bovine serum. The present application instructs that these similar fetuin peptide sequences will also have valuable apoptotic activity. The peptide sequences for FPF 300-09 for other species are:

Human (H-T-F-M-G-V-V-S-L-G; His Thr Phe Met Gly Val Val Ser Leu Gly; SEQ ID NO:3);

Pig (H-S-F-S-G-V-A-S-V-E; His Ser Phe Ser Gly Val Ala Ser Val Glu; SEQ ID NO:4);

Sheep (H-T-F-S-G-V-A-S-V-E; His Thr Phe Ser Gly Val Ala Ser Val Glu; SEQ ID NO:5);

Rat (H-T-F-S-G-V-A-S-V-E; His Thr Phe Ser Gly Val Ala Ser Val Glu; SEQ ID NO:6); and Mouse (H-A-F-S-P-V-A-S-V-E; His Ala Phe Ser Pro Val Ala Ser Val Glu; SEQ ID NO:7). Id.

These analogs are also claimed as being taught by the current application.

DISCUSSION

This invention describes the methods for the isolation of five proteins (Apogen P-1a, Apogen P-1b, Apogen P-1c, Apogen P-2 and Apogen L) that are able to induce apoptosis in prostate cancer cells (Apogen P-1's), in prostate cancer cells and breast cancer cells (Apogen P-2), and leukemia and breast cancer cells (Apogen L), as well as the identification of fetuin as a component of Apogen P-2. The following evidence leads us to believe that these apoptosis-inducing proteins are novel and that they have never been found before: Tumor Necrosis Factor (TNF), Transforming Growth Factor (TGF-Beta), Fas ligand and TRAIL are the proteins reported to induce apoptosis in certain cell lines. (Lin, J. K. et al., Cancer Research 52:385, 1992. Kawakawi, et al., J. of Cellular Physiology 138:1, 1989; Wiley, S. R. et al., Immunity 3:673, 1995; Krammer, et al. "Apoptosis in the APO-1System", Apoptosis: The molecular Basis of Cell Death, Cold Spring Harbor Laboratory Press p. 87, 1991). Evidence suggests that these five proteins are different from any of these known proteins inducing apoptosis as described below:

(1) The activities are different. In our assays, TNF and TGF induced apoptosis in liver cancer cells without effect in prostate cancer (LNCAP) cells even if a very high dose (100 ng/ml) is used. Whereas Apogen P-1's and Apogen P-2 induced apoptosis in prostate cancer rather than in cancer liver cells.

(2) TRAIL and Fas are membrane bound proteins, (Wiley, S. R. et al. Immunity 3:673, 1995; Krammer, et al., "Apoptosis in the APO-1System", Apoptosis: The molecular Basis of Cell Death, Cold Spring Harbor Laboratory Press, p. 87, 1991) whereas the Apogen P-1a, Apogen P-1b, Apogen P-1c, Apogen P-2 and Apogen L are all soluble (non-membrane bound) proteins.

(3) The molecular weights of TNF, TGF and Fas ligand TRAIL are around 17–40 Kd (TNF=17 KD, TGF=24 KD, TRAIL=32 KD, Fas ligand=43 KD) (McGrath, M. H. Clinics in Plastic surgery 17:421, 1993; Wiley, S. R. et al., Immunity 3:673, 1995; Krammer, et al., "Apoptosis in the APO-1System", Apoptosis: The molecular Basis of Cell Death, Cold Spring Harbor Laboratory Press, p. 87, 1991) whereas the molecular weights of Apogen P-1a, Apogen P-1b, Apogen P-1c, Apogen P-2 and Apogen L are between 55–70 Kd.

I claim:

1. A method of preparing a polypeptide having apoptotic activity isolated from fetuin comprising the following steps:

a. Incubating fetuin in solution with a chelating agent;

b. Isolating naked fetuin from step (a);

c. Incubating said naked fetuin in solution with Zinc;

d. Isolating zinc charged fetuin from the solution created in step (c);

e. Drying the zinc charged fetuin from step (d);

f. Dissolving the dried zinc charged fetuin in water to form a solution;

g. Isolating polypeptide containing filtrates from the solution created in step (f) and determining polypeptides which have apoptotic activity in cancer cells.

2. The method of preparing a polypeptide having apoptotic activity isolated from fetuin of claim 1, wherein the chelating agent is 0.1 EDTA.

3. The method of preparing a polypeptide having apoptotic activity isolated from fetuin of claim 1, wherein the Zinc is Zinc Acetate.

4. The method of preparing a polypeptide having apoptotic activity isolated from fetuin of claim 1, wherein isolating naked fetuin from step (a) further comprises using a molecular sieve and centrifugal force.

5. The method of preparing a polypeptide having apoptotic activity isolated from fetuin of claim wherein drying the zinc charged fetuin from step (d) is conducted under a vacuum.

6. The method of preparing a polypeptide having apoptotic activity isolated from fetuin of claim 1, wherein isolating polypeptide containing filtrates from the solution created in step (f) and determining polypeptides which have apoptotic activity in cancer cells further comprises using a molecular sieve with a weight cut-off of 10,000 daltons.

7. The method of preparing a polypeptide having apoptotic activity isolated from fetuin of claim 1, wherein the cancer cells are prostate cancer and colon cancer cells.

* * * * *

UNITED STATES PATENT AND TRADEMARK OFFICE
CERTIFICATE OF CORRECTION

PATENT NO. : 6,720,311 B2
DATED : April 13, 2004
INVENTOR(S) : Tsai

It is certified that error appears in the above-identified patent and that said Letters Patent is hereby corrected as shown below:

Column 23,
Line 6, the number "1" was omitted, should read as follows:
5. The method of preparing a polypeptide having apoptotic activity isolated from fetuin of claim -- 1 --, wherein drying the zinc charged fetuin from step (d) is conducted under a vacuum.

Signed and Sealed this

Sixth Day of July, 2004

JON W. DUDAS
*Acting Director of the United States Patent and Trademark Office*

SEQUENCE LISTING

```
<160> NUMBER OF SEQ ID NOS: 7

<210> SEQ ID NO 1
<211> LENGTH: 10
<212> TYPE: PRT
<213> ORGANISM: Bovine
<222> LOCATION: 300..309
<223> OTHER INFORMATION: Polypeptide fragment from treatment of fetuin
      from bovine sera as described in the specification.

<400> SEQUENCE: 1

His Thr Phe Ser Gly Val Ala Ser Val Glu
1               5                   10

<210> SEQ ID NO 2
<211> LENGTH: 8
<212> TYPE: PRT
<213> ORGANISM: Bovine
<222> LOCATION: 311..317
<223> OTHER INFORMATION: Polypeptide fragment from treatment of fetuin
      from bovine sera as described in the specification.

<400> SEQUENCE: 2

Ser Ala Ser Gly Glu Ala Phe His
1               5
```

```
<210> SEQ ID NO 3
<211> LENGTH: 10
<212> TYPE: PRT
<213> ORGANISM: Human
<222> LOCATION: 300..309
<223> OTHER INFORMATION: Polypeptide fragment from fetuin.

<400> SEQUENCE: 3

His Thr Phe Met Gly Val Val Ser Leu Gly
1               5                   10

<210> SEQ ID NO 4
<211> LENGTH: 10
<212> TYPE: PRT
<213> ORGANISM: Pig
<222> LOCATION: 300..309
<223> OTHER INFORMATION: Polypeptide fragment from fetuin.

<400> SEQUENCE: 4

His Ser Phe Ser Gly Val Ala Ser Val Glu
1               5                   10

<210> SEQ ID NO 5
<211> LENGTH: 10
<212> TYPE: PRT
<213> ORGANISM: Sheep
<222> LOCATION: 300..309
<223> OTHER INFORMATION: Polypeptide fragment from fetuin.

<400> SEQUENCE: 5

His Thr Phe Ser Gly Val Ala Ser Val Glu
1               5                   10

<210> SEQ ID NO 6
<211> LENGTH: 10
<212> TYPE: PRT
<213> ORGANISM: Rat
<222> LOCATION: 300..309
<223> OTHER INFORMATION: Polypeptide fragment from fetuin.

<400> SEQUENCE: 6

His Thr Phe Ser Gly Val Ala Ser Val Glu
1               5                   10

<210> SEQ ID NO 7
<211> LENGTH: 10
<212> TYPE: PRT
<213> ORGANISM: Mouse
<222> LOCATION: 300..309
<223> OTHER INFORMATION: Polypeptide fragment from fetuin.

<400> SEQUENCE: 7

His Ala Phe Ser Pro Val Ala Ser Val Glu
1               5                   10
```